United States Patent [19]
Waschutza et al.

[11] Patent Number: 6,046,034
[45] Date of Patent: Apr. 4, 2000

[54] THERMOSTABLE VARIANTS OF HUMAN INTERFERON-γ(IFN-γ)

[75] Inventors: Gero Waschutza, Meinersen; Volkhart Li, Cologne; Bernd Otto, Hannover, all of Germany

[73] Assignee: Fraunhofer-Gesellschaft zur Forderung der Angewandten Forschung E. V., Munich, Germany

[21] Appl. No.: 09/029,819

[22] PCT Filed: Aug. 15, 1996

[86] PCT No.: PCT/DE96/01556

§ 371 Date: May 11, 1998

§ 102(e) Date: May 11, 1998

[87] PCT Pub. No.: WO97/24376

PCT Pub. Date: Jul. 10, 1997

[30] Foreign Application Priority Data

Sep. 18, 1995 [DE] Germany .............. 195 35 863

[51] Int. Cl.⁷ .............. C12P 21/04; C07K 21/04; C07K 1/00; A61K 38/21
[52] U.S. Cl. .................. 435/69.51; 536/23.52; 530/351; 424/85.5; 435/325; 435/252.3; 435/252.33; 435/320.1
[58] Field of Search .............. 536/23.52; 530/351; 424/85.5; 435/69.51, 325, 252.3, 252.33, 320.1

[56] References Cited

FOREIGN PATENT DOCUMENTS 0 170 917 A1  2/1986  European Pat. Off. .
0 306 870 A2  3/1989  European Pat. Off. .
92/08737  5/1992  WIPO .

OTHER PUBLICATIONS

Modelling of Interhelical Contacts in Interferons–β, –γ, and Dimeric Interleukin–5, Biochemical and Biophysical Research Communications, vol. 201, No. 3, Jun. 30, 1994, pp. 1401–1405.

Expression of human immune interferon cDNA in E.coli and monkey cells, Nature, vol. 295, Feb. 11, 1982, pp. 503–508.

Molecular cloning of human immune interferon cDNA and its expression in eukaryotic cells, Nucleic Acids Research, vol. 10, No. 8, 1982, pp. 2487–2501.

Three–Dimensional Structure of Recombinant Human Interferon–γ, Science, vol. 252, May 3, 1991, pp. 698–702.

*Primary Examiner*—David L. Fitzgerald
*Attorney, Agent, or Firm*—Barnes & Thornburg

[57] ABSTRACT

The invention provides new variants of recombinant human interferon-γ (rhIFN-γ), vectors and host cells for their production, and therapeutic methods employing them. The variants are characterized by the substitution of one or more pairs of amino acids selected from $Glu^8$-$Ser^{70}$, $Ala^{18}$-$His^{112}$, $Lys^{81}$ $Leu^{121}$, and $Gln^{49}$-$Leu^{96}$ by pairs of Cys residues, and optionally by the deletion of from one to ten amino acid residues from C-terminus of the native IFN-γ sequence. The variants of the invention exhibit greater thermal stability and no loss of biological activity as compared to native-sequence rhIFN-γ.

20 Claims, 4 Drawing Sheets

Fig. 1

| | | | | | | | | | | | | |
|---|---|---|---|---|---|---|---|---|---|---|---|---|
| Gln | Asp | Pro | Tyr | Val | Lys | Glu | Ala | Glu | Asn | Leu | Lys | Lys |
| 1 | | | | 5 | | | | | 10 | | | |
| Tyr | Phe | Asn | Ala | Gly | His | Ser | Asp | Val | Ala | Asp | Asn | Gly |
| | 15 | | | | | 20 | | | | | 25 | |
| Thr | Leu | Phe | Leu | Gly | Ile | Leu | Lys | Asn | Trp | Lys | Glu | Glu |
| | | | 30 | | | | | 35 | | | | |
| Ser | Asp | Arg | Lys | Ile | Met | Gln | Ser | Gln | Ile | Val | Ser | Phe |
| 40 | | | | | 45 | | | | | 50 | | |
| Tyr | Phe | Lys | Leu | Phe | Lys | Asn | Phe | Lys | Asp | Asp | Gln | Ser |
| | | 55 | | | | | 60 | | | | | 65 |
| Ile | Gln | Lys | Ser | Val | Glu | Thr | Ile | Lys | Glu | Asp | Met | Asn |
| | | | | 70 | | | | | 75 | | | |
| Val | Lys | Phe | Phe | Asn | Ser | Asn | Lys | Lys | Lys | Arg | Asp | Asp |
| | 80 | | | | | 85 | | | | | 90 | |
| Phe | Glu | Lys | Leu | Thr | Asn | Tyr | Ser | Val | Thr | Asp | Leu | Asn |
| | | | 95 | | | | | 100 | | | | |
| Val | Gln | Arg | Lys | Ala | Ile | His | Glu | Leu | Ile | Gln | Val | Met |
| 105 | | | | | 110 | | | | | 115 | | |
| Ala | Glu | Leu | Ser | Pro | Ala | Ala | Lys | Thr | Gly | Lys | Arg | Lys |
| | | 120 | | | | | 125 | | | | | 130 |
| Arg | Ser | Gln | Met | Leu | Phe | Arg | Gly | Arg | Arg | Ala | Ser | Gln |
| | | | | 135 | | | | | 140 | | | 143 |

Fig. 2

Met Gln Asp Pro Tyr Val Lys Xaa Ala Glu Asn Leu Lys
1             5             10

Lys Tyr Phe Asn Xba Gly His Ser Asp Val Ala Asp Asn
    15            20                    25

Gly Thr Leu Phe Leu Gly Ile Leu Lys Asn Trp Lys Glu
            30                35

Glu Ser Asp Arg Lys Ile Met Gln Ser Xda Ile Val Ser
40                45                50

Phe Tyr Phe Lys Leu Phe Lys Asn Phe Lys Asp Asp Gln
        55                60                    65

Ser Ile Gln Lys Xab Val Glu Thr Ile Lys Glu Asp Met
                70                75

Asn Val Xca Phe Phe Asn Ser Asn Lys Lys Lys Arg Asp
    80                85                    90

Asp Phe Glu Lys Xdb Thr Asn Tyr Ser Val Thr Asp Leu
            95                100

Asn Val Gln Arg Lys Ala Ile Xbb Glu Leu Ile Gln Val
105               110               115

Met Ala Glu Xcb Ser Pro Ala Ala Lys Thr Gly Lys Arg
        120               125                   130

Lys Arg Ser Gln Met Leu Phe Arg Gly Arg Arg Ala Ser
            135               140

Gln
144

Fig. 3

| | | | | | | | | | | |
|---|---|---|---|---|---|---|---|---|---|---|
| Met 1 | Gln | Asp | Pro | Tyr 5 | Val | Lys | Xaa | Ala | Glu 10 | Asn | Leu | Lys |
| Lys | Tyr 15 | Phe | Asn | Xba | Gly 20 | His | Ser | Asp | Val | Ala 25 | Asp | Asn |
| Gly | Thr | Leu | Phe 30 | Leu | Gly | Ile | Leu | Lys 35 | Asn | Trp | Lys | Glu |
| Glu 40 | Ser | Asp | Arg | Lys | Ile 45 | Met | Gln | Ser | Xda | Ile 50 | Val | Ser |
| Phe | Tyr | Phe 55 | Lys | Leu | Phe | Lys | Asn 60 | Phe | Lys | Asp | Asp | Gln 65 |
| Ser | Ile | Gln | Lys | Xab 70 | Val | Glu | Thr | Ile | Lys 75 | Glu | Asp | Met |
| Asn | Val | Xca 80 | Phe | Phe | Asn | Ser | Asn 85 | Lys | Lys | Lys | Arg 90 | Asp |
| Asp | Phe | Glu | Lys 95 | Xdb | Thr | Asn | Tyr | Ser | Val 100 | Thr | Asp | Leu |
| Asn 105 | Val | Gln | Arg | Lys | Ala 110 | Ile | Xbb | Glu | Leu | Ile 115 | Gln | Val |
| Met | Ala | Glu | Xcb 120 | Ser | Pro | Ala | Ala 125 | Lys | Thr | Gly | Lys | Arg 130 |
| Lys | Arg | Ser | Xea 134 | | | | | | | | | |

Fig. 4

```
for Xaa:  TAAGGTTTTC  TGCACATTTT  ACATATGGG         29
    or    TAAGGTTTTC  TGCGCATTTT  ACATATGGG         29 for Xab:  TGATGGTCTC  CACACACTTT  TGGATGCTC         29
    or    TGATGGTCTC  CACGCACTTT  TGGATGCTC         29 for Xba:  CATCTGAATG  ACCGCAATTA  AAATATTTC         29
    or    CATCTGAATG  ACCACAATTA  AAATATTTC         29 for Xbb:  ACTTGGATGA  GTTCGCATAT  TGCTTTGCG         29
    or    ACTTGGATGA  GTTCACATAT  TGCTTTGCG         29 for Xca:  TGCTATTGAA  AAAACAGACA  TTCATGTCT         29
    or    TGCTATTGAA  AAAGCAGACA  TTCATGTCT         29 for Xcb:  TAGCTGCTGG  CGAACATTCA  GCCATCACT         29
    or    TAGCTGCTGG  CGAGCATTCA  GCCATCACT         29 for Xda:  AAAAGGAGAC  AATGCAGCTC  TGCATTATT         29
    or    AAAAGGAGAC  AATACAGCTC  TGCATTATT         29 for Xdb:  CCGAATAATT  AGTGCACTTT  TCGAAGTCA         29
    or    CCGAATAATT  AGTACACTTT  TCGAAGTCA         29
```

THERMOSTABLE VARIANTS OF HUMAN INTERFERON-γ(IFN-γ)

CROSS-REFERENCE TO RELATED APPLICATIONS

This application is a U.S. national application of international application Ser. No. PCT/DE96/01556, filed Aug. 15, 1996, which claims priority to German serial No.195 35 853.8, filed Sep. 18, 1995.

The invention relates to variants of the human recombinant interferon-γ with increased thermal stability.

Interferon-γ is suitable as an antiviral, antiproliferative, immunomodulatory human therapeutic agent, particularly for the treatment of kidney tumours and chronic granulomatosis.

Like the interleukins, interferons belong to the class of the cytokines and are listed in various classes: interferon-α, interferon-β, interferon-γ, interferon-ω and interferon-τ. Interferon-γ is a glycoprotein, whose amino acid sequence has been known since 1982 (Nucl. Acid Res. 10, pages 2487 and following (1982)). In the mature condition the interferon-γ has 143 amino acids and a molecular weight of 63 to 73 kilodaltons. The amino acid sequence of interferon-γ is shown in FIG. 1. It will be noticed that the sequence contains no cystein.

The tertiary and quaternary structure of the non-glycosylised protein was clarified in 1991 (Science 252, page 698 and following (1991)). According to this, interferon-γ exists as a homodimer, the monomers being orientated in contrary directions in such a way that the C-terminal end of one monomer is located in the vicinity of the N-terminal end of the other monomer. Each of these monomers in all has six α-helices.

Interferon-γ is also called immunointerferon, as it has non-specific antiviral, antiproliferative and in particular immunomodulatory effects. Its production in T-helper-lymphocytes is stimulated by mitogens and antigens. The effect of the expressed interferon-γ has not yet been precisely clarified, but is subject to intensive research. In particular, interferon-γ leads to the activation of macrophages and to the synthesis of histocompatability antigens of the class 2. In vitro, the activity of interferon-γ is normally determined as a reduction in the virus-induced cytopathic effect, which arises from treatment with interferon-γ. Due to its antigen-non-specific antiviral, antiproliferative and immunomodulatory activity it is suitable as a human therapeutic agent, for example of kidney tumours and chronic granulomatosis. Clinical studies of various tumours are being carried out at present. Great expectations are set also on the interferon-γ therapy of neurodermitis. Furthermore, interferon-γ is used in the research field also as a fine chemical for example for the stimulation of cell cultures or for determining interferon levels.

Since 1982 it has been possible to express variants of the human interferon-γ in bacteria such as escherichia coli (Nature 295, pages 503 and following (1982)). The monomer of these recombinant variants of the human interferon-γ has, in addition to the 143 amino acids of the native human monomer, an additional N-terminal methionin as an additional amino acid. This recombinant human interferon-γ (rhu-IFN-γ) is not glycosylised. It can be obtained in large quantities and was therefore extremely accurately characterised.

The recombinant human interferon-γ also exists as a dimer and has normal biological activity. It is acid-sensitive and temperature-sensitive with a melting point of 52° C.

Of all the interferons, the thermal stability of human interferon-γ is the lowest. This low thermal stability of interferon-γ renders it difficult to use as a human therapeutic agent.

Tests were carried out at an early stage in order to generate variants with improved properties of the recombinant human interferon-γ with the aid of molecular-biological methods. In EP 0 306870 A2, variants of recombinant human interferon-γ were presented, whose activity was significantly increased by splitting off the C-terminal 7–11 amino acids. In addition, WO 92-08737 indicates a variant of recombinant human interferon-γ (Interferon-γ C-10L) which has an increased biological activity. However, in none of these variants of recombinant interferon-γ was the thermal stability significantly increased. Therefore the low thermal stability also renders difficult the use of these proteins as a human therapeutic agent.

The object of the present invention is to make available variants of the recombinant human interferon-γ whose thermal stability is increased, the biological activity being similar, preferably equal to or even better than that of the unaltered recombinant human interferon-γ. It is a further object of this invention to indicate gene sequences, vectors with gene sequences and micro-organisms with gene sequences which can be used to manufacture the expression system and the variant according to the invention of interferon-γ.

This object is achieved in that there are indicated DNA sequences and recombinant vectors with such DNA sequences, for example plasmids and bacteriophages, and micro-organisms which contain such DNA sequences, which code for polypeptides, which are characterised in comparison to recombinant human interferon-γ by increased thermal stability. Furthermore, methods are indicated by means of which such DNA sequences, recombinant vectors and micro-organisms can be produced. With the aid of the oligonucleotides according to the invention and corresponding restriction endonucleases, on the basis of a plasmid known per se, which contains the gene for recombinant human interferon-γ, recombinant vectors such as plasmids or bacteriophages and micro-organisms can be produced, which contain a DNA sequence which codes for the polypeptides according to the invention.

There is further indicated a manufacturing method for the proteins according to the invention, by means of which, with the aid of the micro-organisms according to the invention the proteins according to the invention can be obtained, concentrated and cleaned up, and uses of the proteins according to the invention as a human therapeutic agent or/and fine chemical.

The polypeptides according to the invention consist of a sequence of 144 amino acids, made up of the sequence of the 143 amino acids of the recombinant human interferon-γ and an additional N-terminal methionin. Otherwise the polypeptide according to the invention differs from the monomer of the recombinant human interferon-γ in that at least one pair of amino acids from four predetermined amino acid pairs is exchanged for cystein. These four amino acid pairs are Glu8 and Ser70, Ala18 and His112, Lys81 and Leu121 and Gln49 and Leu96. The complete amino acid sequence is given for the recombinant human interferon-γ in FIG. 1 and for the polypeptide according to the invention in FIG. 2. In this case Xaa means Glu8, Xab Ser70, Xba Ala18, Xbb His112, Xca Lys81, Xcb Leu121, Xda Gln49 and Xdb Leu 96, insofar as these amino acids do not stand for cystein in the polypeptide according to the invention.

It became surprisingly apparent that the proteins according to the invention have higher thermal stability in comparison to recombinant human interferon-γ.

The proteins according to the invention are probably, like recombinant human interferon-γ, homodimers, whose monomers are so oriented that the N-terminal end of one monomer is located in the vicinity of the C-terminal end of the other monomer. Possibly the exchange in pairs of the amino acids leads to additional intermonomeric and intramonomeric disulphide bridges. Thus the exchange of Ala18 and His112 and the exchange of Lys80 and Leu120 probably leads to intermonomeric disulphide bridges, and the exchange of Glu8 and Ser70 to an intramonomeric disulphide bridge, while the exchange of Glu49 and Leu96 does not lead to any additional covalent bond. Clearly the introduction of cystein pairs into the amino acid sequence of the polypeptide monomer cannot lead to a direct conclusion regarding the formation of disulphide bridges.

Due to the improved properties of the proteins and polypeptides according to claims 1, 2 and 3 compared to the previous recombinant human interferon-γ, these proteins are particularly suitable for various forms of application as a human therapeutic agent. They are usable with advantage particularly in those areas in which previously recombinant human interferon-γ was used as a medicinal drug, such for example as kidney tumours or chronic granulomatosis. It is further to be expected that the proteins according to the invention can be used in all future indications in which previous recombinant human interferon-γ will be used as a medicinal drug.

The variants according to the invention of the recombinant human interferon-γ are also suitable for use as fine chemical for example for in vitro tests, in order to determine interferon levels and for the stimulation of cell cultures. Due to their higher thermal stability and thus their improved handling, and due to their antiviral, antiproliferative and immunomodulatory biological activity, they can replace previous recombinant human interferon-γ in all areas where the latter is used.

Further advantageous embodiments are illustrated in the dependent claims.

A shortening of the C-terminal end of the polypeptide monomer by one to ten amino acids leads to an improvement in the biological activity. In this way both the thermal stability of the variants according to the invention of the recombinant human interferon-γ and also its biological activity are improved in comparison to recombinant human interferon-γ.

The production of the new recombinant vectors and micro-organisms will be described in the following.

In order to produce a recombinant micro-organism which contains a gene sequence which codes for one of the polypeptides according to the invention, the sequence of the human recombinant interferon-γ is cut with the aid of restriction endonucleases from a vector which contains this sequence, and cloned into the DNA of a phage. The phage DNA is then mutated with the aid of appropriate oligonucleotides, so that it codes for one of the polypeptides according to the invention. The genetically altered phage is then multiplied and the altered sequence for human recombinant interferon-γ is cut out of the DNA of the phage with the aid of the same restriction endonucleases, and cloned back into the plasmid. With the aid of this plasmid, a micro-organism is now transfected, which can then express the new gene coding for the polypeptide according to the invention.

This method will now be illustrated by the example of a transfected bacterium escherichia coli K12 strain JM 105.

The known plasmid pKK-233-2/IFN-γ was used as an outset material. This plasmid was digested with the restriction endonucleases EcoRI and HindIII. This plasmid has between the two intersections for EcoRI and HindIII the gene for human recombinant interferon-γ and a strong IPTG-inducable trc-promoter. This DNA section with a length of 751 base pairs was then likewise cloned with EcoRI and HindIII into the likewise known bacteriophage M13mp18. Then the DNA of the bacteriophage was mutated with methods known per se and appropriate oligonucleotides in such a way that the gene for interferon-γ codes for one of the variants according to the invention. This new bacteriophage M13mp18/IFN-γ was multiplied in the bacterium escherichia coli K12 strain TG1. The now altered sequence section, which contained the gene for the altered rhu-IFN-γ was cut out from the c-DNA of the multiplied phage with the aid of the same restriction endonucleases EcoRI and HindIII, and cloned back into the plasmid pKK233-2. This now likewise altered plasmid pKK233-2/IFN-γ was now used to transfect the bacterium escherichia coli K12 strain JM105.

The oligonucleotides used have a length of 29 base pairs and a sequence which is complementary to the single-strand DNA sequence of the corresponding bacteriophage DNA which contains roughly centrally the base pairs to be mutated. Both ACA and GCA were used as a complementary codon for the amino acid cystein to be introduced. These oligonucleotide primers were produced with a commercially available DNA synthesiser. No difference was found in the mutation rate between the two codons for cystein.

In order to produce the proteins according to the invention, the transformed recombinant micro-organism is cultivated and then the protein according to the invention is separated, cleaned up and concentrated from the culture.

The production method for the proteins according to the invention will now be illustrated by way of example with reference to the abovementioned transfected escherichia coli K13 strain JM105.

The transfected bacteria contain the gene sequence for the altered interferon-γ and a trc promotor inducible by IPTG. The bacteria are taken in cultures and expression of the mutated interferon-γ is induced by addition of IPTG. The expressed altered interferon-γ is stored by the bacteria cells in so-called "inclusion bodies". In order to clean the expressed altered interferon-γ, the bacteria cells after successful expression are opened and the "inclusion bodies" are freed of soluble bacterial proteins by multiple washing. The opening is undertaken preferably mechanically, for example by ultrasound. The protein according to the invention is brought into solution by a denaturing step with guanidine hydrochloride and separated. Then the protein according to the invention is renatured by dilution in a phosphate buffer, and folded into its biologically active form. The interferon-γ, in this way pure to more than 90%, is obtained at a rate of up to 30% of the total protein content of the *E.coli* culture. It can then be concentrated and further purified by an affinity chromatography on a column or in a batch-like process and after a further filtration step, e.g. an HPLC-gel filtration, achieves a purity of more than 95%.

A batch-like process in the sense of this invention, also known as a batch method, is understood to mean the following: the chromatographic material is regularly stirred into a solution of the protein according to the invention in such a way that the altered interferon-γ is uniformly distributed and bonds to the chromatographic material and the interferon-γ protein concentration comes to no more than about 2 mg/ml packed chromatographic material. The chromatographic material laden with interferon-γ is washed in the batch with phosphate buffer and the altered interferon-γ is then eluated in the batch with a saline solution in the phosphate buffer. In this case for example, SP-sepharose or Affi-gel-blue can be used as chromatographic material.

The figures show:

FIG. 1: the amino acid sequence of the human recombinant human interferon-γ (SEQ ID NO: 1);

FIG. 2: the amino acid sequence of the variant of the recombinant human interferon-γ according to claim 1 (SEQ ID NO: 2);

FIG. 3: the amino acid sequence of the variants of the recombinant human interferon-γ according to claim 2; and FIG. 4: the base sequence of the oligonucleotides, which were used to produce the recombinant DNA which codes for the proteins according to the invention.

Some embodiments of the invention, given by way of example, will be explained in the following.

EXAMPLE 1

The amino acids Glu8 and Ser70 were exchanged according to the following method and a correspondingly altered interferon-γ was produced.

The interferon-γ gene of the plasmid pKK-233-2/IFN-γ was recloned in the phages M13mp18. For this purpose a plasmid preparation was digested with the restriction endonucleases EcoRI and HindIII. By means of this digestion, the vector was split into two fragments with the lengths 751 base pairs and 4305 base pairs. Both fragments were separated from one another via a 1% agarose gel, and the corresponding bands, of a size of 751 base pairs, were cut out from the gel and isolated. This fragment contained, in addition to the complete interferon-γ-gene, also the trc-promoter and further vector ingredients at the 5' end.

A 150 ml culture of escherichia coli TG1 was infected with the phage M13mp18. After incubation for 5 hours, the cells were centrifuged off, resuspended once and again pelletised. The double-strand circular phage DNA was cleaned up by the Quiagen™ plasmid isolation kit (Diagen Company) from the cells. The RF-DNA of the phage M13mp18 was likewise digested with the restriction enzymes EcoRI and HindIII and cleaned via a 1% agarose gel. Then the isolated EcoRI/HindIII insert, 751 bp long, was cloned from the vector pKK-233-2/IFN-γ in the phages M13mp18.

In order to produce expression vectors for the new variant of the interferon-γ, mutations of the DNA sequence were carried out at specific points. The method is based on hybridisation of an oligonucleotide with the desired target sequence on single-strand DNA (ssDNA) of the phage M13 to be altered. In order to produce the two spot mutations of Glu8 and Ser70 to cystein, the following oligonucleotides were used:

for the mutation of Glu8 to Cys

TAAGGTTTTC TGCACATTTT ACATATGGG 29   (SEQ ID NO:4)

or

-continued
TAAGGTTTTC TGCGCATTTT ACATATGGG 29   (SEQ ID NO:5)

and for mutation of Ser70 to Cys

TGATGGTCTC CACACACTTT TGGATGCTC 29   (SEQ ID NO:6)

oder

TGATGGTCTC CACGCACTTT TGGATGCTC 29   (SEQ ID NO:7)

The oligonucleotides were produced with the aid of a commercially available synthesiser. The two codons for cystein are TGT and TGC. The corresponding complementary base sequence in the nucleotide strand is GCA or ACA. Both codons were used (emphasised). As a length for oligonucleotide primers, that of 29 base pairs was selected. All the nucleotides had to be phosphorylised at their 5' end with T4-polynucleotidekinase for the mutagenesis.

Independently of the sequence of the oligonucleotides, hybridisation was carried out at 80° C. in a water bath. After execution of the in vitro mutagenesis, the transformation of the double-strand RF form of the phage DNA was carried analogously to a normal plasmid with the CaCl$_2$ method. Cells of E.coli were added to the recombinant phage-RF-DNA, IPTG and X-Gal and plated out. After overnight incubation at 37° C. fourteen phage clones were respectively picked from each mutagenesis reaction and again incubated together with E.coli for five hours at 37° C.

The sequence monitoring of the mutated cDNA of the bacteriophages, which is intended to code for the new variant of the recombinant interferon-γ, was effected by didesoxy-sequencing, with the T7-sequencing kit of Pharmacia. Thus the desired mutations were confirmed.

Following the mutagenesis of the phage-DNA, the sequence 751 bp long, which coded for the altered rhu-IFN-γ, was cut out from the phage DNA with the aid of the same restriction endonucleases, EcoRI and HindIII and cloned back into the phages pKK233-2. The bacterium escherichia coli K12 strain JM105 was then transfected with this plasmid.

Expression of the altered interferon-γ was then carried out according to the methods described above. The biological, antiviral activity of the altered interferon-γ was determined by the reduction in the virus-induced cytopathic effect which resulted after treatment with the altered interferon-γ. Human lung fibroblasts A549 were used as a cell strain, and as a virus the encephalomyocarditis virus.

Analysis of the altered interferon-γ obtained showed that its biological activity was unaltered in comparison to recombinant human interferon-γ. In contrast to recombinant human interferon-γ with a melting temperature of 52.5° C., the melting temperature of the new variant was considerably increased at 68.5° C. With an identical biological activity, there consequently resulted for the new variant of interferon-γ a considerably improved thermal stability in comparison to unaltered interferon-γ.

EXAMPLE 2

A variant of the recombinant human interferon-γ was produced in which the two amino acids Ala18 and His112 were exchanged for cystein. Production of the corresponding DNA, phage DNA, plasmid DNA and the corresponding expression organisms was carried out as in Example 1. The following oligonucleotides were used for hybridisation of the ssDNA:

for the mutation of Ala18 to Cys

CATCTGAATG ACCGCAATTA AAATATTTC 29 (SEQ ID NO:8)

or

CA TCTGAATG ACCACAATTA AAATATTTC 29 (SEQ ID NO:9)

and for mutation of His112 to Cys

ACTTGGATGA GTTCGCATAT TGCTTTGCG 29 (SEQ ID NO:10)

or

ACTTGGATGA GTTCACATAT TGCTTTGCG 29 (SEQ ID NO:11)

In this variant of recombinant human interferon-γ also there was an increased thermal stability with a melting point of the interferon-γ of 78.6° C. with simultaneous indication of antiviral activity of the new variant.

EXAMPLE 3

A variant of the recombinant human interferon-γ was produced in which the two amino acids Lys81 and Leu121 were exchanged for cystein. Production of the corresponding DNA, plasmid-DNA, phage-DNA and of the corresponding expression micro-organism was effected as described in Example 1. The following oligonucleotides were used to produce the variant:

for the mutation of Lys81 to Cys

TGCTATTG-KA AAAACAGACA TTCATGTCT 29 (SEQ ID NO:12)

or

TGCTATTGAA AAAGCAGACA TTCATGTCT 29 (SEQ ID NO:13)

and for mutation of Leu121 to Cys

TAGCTGCTGG CGAACATTCA GCCATCACT 29 (SEQ ID NO:14)

or

TA GCTGCTGG CGAGCATTCA GCCATCACT 29 (SEQ ID NO:15)

for the mutation of Gln49 to Cys

AAAAGGAGAC A.ATGCAGCTC TGCATTATT 29 (SEQ ID NO:16)

or

AAAAGGAGAC AATACAGCTC TGCATTATT 29 (SEQ ID NO:17)

This variant of the recombinant human interferon-γ revealed a biological antiviral activity similar to that of the unaltered recombinant interferon-γ with improved thermal stability.

EXAMPLE 4

A variant of the recombinant interferon-γ was produced in which the two amino acids Gln49 and Leu96 were exchanged for cystein. Production of the corresponding DNA, plasmid-DNA, phage-DNA and of the corresponding expression micro-organism was carried out likewise as described in Example 1. The following oligonucleotides were used to produce this variant of interferon-γ:

for the mutation of Gln49 to Cys

AAAAGGAGAC AATGCAGCTC TGCATTATT 29 (SEQ ID NO:16)

or

AAAAGGAGAC AATACAGCTC TGCATTATT 29 (SEQ ID NO:17)

and for mutation of Leu96 to Cys

CCGAATAATT AGTGCACTTT TCGAAGTCA 29 (SEQ ID NO:18)

or

CCGAATAATT AGTACACTTT TCGAAGTCA 29 (SEQ ID NO:19)

For this variant of interferon-γ also the advantages illustrated in the previous Examples resulted. In this case also this variant of interferon-γ with an antiviral activity which corresponds to about 30% of the unaltered recombinant human interferon-γ, is suitable for the applications according to the invention as a therapeutic agent or as a fine chemical such for example as for the stimulation of cell cultures.

EXAMPLE 5

A variant of the altered recombinant human interferon-γ shown in Example 1 was produced, in which the amino acids Glu8 and Ser70 were exchanged for cystein, and in which in addition, in an otherwise known way, the amino acid sequence of the monomeric polypeptide C-terminal was shortened by 10 amino acids.

With increased thermal stability, this variant of the recombinant human interferon-γ reveals an activity which lies 1–4 times higher than the antiviral activity of the unaltered recombinant human interferon-γ. Thus a variant of interferon-γ is presented which, in addition to increased thermal stability, simultaneously shows increased biological activity.

We claim:

1. A substituted interferon-gamma (IFN-γ) protein comprising:

(a) a polypeptide comprising the amino acid sequence of SEQ ID NO: 2 wherein
Xaa at position 8 is Glu or Cys,
Xaa at position 70 is Ser or Cys,
Xaa at position 18 is Ala or Cys,
Xaa at position 112 is His or Cys,
Xaa at position 81 is Lys or Cys,
Xaa at position 121 is Leu or Cys,
Xaa at position 49 is Gln or Cys, and
Xaa at position 96 is Leu or Cys,
wherein Cys residues are present at both positions of at least one pair selected from the group consisting of positions 8 and 70, 18 and 112, 81 and 121, and 49 and 96;

(b) a polypeptide which differs from a polypeptide according to (a) by the deletion of 1 to 10 amino acids from the C-terminus; or (c) a homodimer of a polypeptide according to (a) or (b).

2. A DNA molecule comprising a sequence that codes for a polypeptide according to claim 1.

3. A recombinant vector, comprising a DNA sequence that codes for a polypeptide according to claim 1.

4. The recombinant vector of claim 3, wherein the vector is a plasmid.

5. The recombinant vector of claim 4, wherein the plasmid is pKK233-2.

6. The recombinant vector of claim 3, wherein the vector is a bacteriophage.

7. The recombinant vector of claim 6, wherein the bacteriophage is M13mp18.

8. A recombinant micro-organism, transformed with a vector according to one of claims 3 to 7.

9. The recombinant micro-organism of claim 8, wherein the micro-organism is a bacterium.

10. The recombinant micro-organism of claim 9, wherein the bacterium is *Escherichia coli* K12 strain JM105.

11. A method of producing the recombinant bacteriophage of claim 6 or 7, said method comprising the steps of digesting plasmid pKK233-2 containing an IFN-γ-encoding insert with a restriction endonuclease, inserting the resulting DNA section coding for IFN-γ into the DNA of bacteriophage M13mp18, and modifying the IFN-γ coding sequence to encode said substituted IFN-γ polypeptide.

12. The method of claim 11, wherein the plasmid is digested with the restriction endonucleases EcoR1 and HindIII.

13. A method of producing a recombinant bacterium comprising the step of transfecting a bacterial cell with the plasmid of claim 4 or 5.

14. A method of producing the polypeptide of claim 1, said method comprising the steps of cultivating a bacterium, transformed with a vector according to one of claims 3 to 7, breaking open said transformed bacterium and isolating the polypeptide.

15. The method of claim 14, wherein the bacteria cells are disrupted mechanically.

16. The method of claim 14 wherein the isolation of the polypeptide comprises the steps of washing the bacterial cell vesicles which contain the polypeptide, solubilizing the polypeptide with guanidinium hydrochloride, diluting the resulting solution, and renaturing the polypeptide.

17. The method of claim 16, wherein the polypeptide is further isolated by column or batch affinity chromatography followed by gel filtration.

18. The method of claim 17, wherein batch affinity chromatography is conducted by bringing an affinity matrix into uniform contact with a solution containing the polypeptide, washing the matrix, and eluting the polypeptide from the matrix in batch format.

19. The method of claim 18, wherein the affinity chromatography matrix is SP-SEPHAROSE™ or AFFI-GEL BLUE™.

20. A method of treating a patient having at least one of a kidney rumor, chronic granulomatosis and neurodermatitis, said method comprising the step of administering to said patient an effective amount of a composition comprising a substituted IFN-γ protein according to claim 1.

* * * * *

UNITED STATES PATENT AND TRADEMARK OFFICE
CERTIFICATE OF CORRECTION

PATENT NO. : 6,046,034
DATED : April 4, 2000
INVENTOR(S) : Gero Waschutza, Bernd Otto It is certified that error appears in the above-identified patent and that said Letters Patent is hereby corrected as shown below:

On the bibliography page, left hand column,
Delete "[87] PCT Pub. No. WO97/24376" and insert in its place -- [87] PCT Pub. No. WO97/11179--; and Delete "[30] Foreign Application Priority Data Sep. 18, 1995
[DE] Germany ......195 35 863" and insert in its place -- [30] Foreign Application Priority Data Sep. 18, 1995 [DE] Germany ......195 35 853--.

Signed and Sealed this

Nineteenth Day of June, 2001

Attest:

NICHOLAS P. GODICI
Attesting Officer
Acting Director of the United States Patent and Trademark Office

SEQUENCE LISTING

<160> NUMBER OF SEQ ID NOS: 19

<210> SEQ ID NO 1
<211> LENGTH: 143
<212> TYPE: PRT
<213> ORGANISM: Homo sapiens

<400> SEQUENCE: 1

-continued

```
Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg Ala Ser Gln
        130                 135                 140
```

<210> SEQ ID NO 2
<211> LENGTH: 144
<212> TYPE: PRT
<213> ORGANISM: Homo sapiens
<220> FEATURE:
<221> NAME/KEY: SITE
<222> LOCATION: (8)
<223> OTHER INFORMATION: Xaa = Glu or Cys
<220> FEATURE:
<221> NAME/KEY: SITE
<222> LOCATION: (18)
<223> OTHER INFORMATION: Xaa = Ala or Cys
<220> FEATURE:
<221> NAME/KEY: SITE
<222> LOCATION: (49)
<223> OTHER INFORMATION: Xaa = Gln or Cys
<220> FEATURE:
<221> NAME/KEY: SITE
<222> LOCATION: (70)
<223> OTHER INFORMATION: Xaa = Ser or Cys
<220> FEATURE:
<221> NAME/KEY: SITE
<222> LOCATION: (81)
<223> OTHER INFORMATION: Xaa = Lys or Cys
<220> FEATURE:
<221> NAME/KEY: SITE
<222> LOCATION: (96)
<223> OTHER INFORMATION: Xaa = Leu or Cys
<220> FEATURE:
<221> NAME/KEY: SITE
<222> LOCATION: (112)
<223> OTHER INFORMATION: Xaa = His or Cys
<220> FEATURE:
<221> NAME/KEY: SITE
<222> LOCATION: (121)
<223> OTHER INFORMATION: Xaa = Leu or Cys

<400> SEQUENCE: 2

```
Met Gln Asp Pro Tyr Val Lys Xaa Ala Glu Asn Leu Lys Lys Tyr Phe
 1               5                  10                  15

Asn Xaa Gly His Ser Asp Val Ala Asp Asn Gly Thr Leu Phe Leu Gly
             20                  25                  30

Ile Leu Lys Asn Trp Lys Glu Glu Ser Asp Arg Lys Ile Met Gln Ser
         35                  40                  45

Xaa Ile Val Ser Phe Tyr Phe Lys Leu Phe Lys Asn Phe Lys Asp Asp
 50                  55                  60
```

```
Gln Ser Ile Gln Lys Xaa Val Glu Thr Ile Lys Glu Asp Met Asn Val
 65                  70                  75                  80

Xaa Phe Phe Asn Ser Asn Lys Lys Arg Asp Asp Phe Glu Lys Xaa
                 85                  90                  95

Thr Asn Tyr Ser Val Thr Asp Leu Asn Val Gln Arg Lys Ala Ile Xaa
            100                 105                 110

Glu Leu Ile Gln Val Met Ala Glu Xaa Ser Pro Ala Ala Lys Thr Gly
            115                 120                 125

Lys Arg Lys Arg Ser Gln Met Leu Phe Arg Gly Arg Arg Ala Ser Gln
    130                 135                 140
```

<210> SEQ ID NO 3
<211> LENGTH: 143
<212> TYPE: PRT
<213> ORGANISM: Homo sapiens
<220> FEATURE:
<221> NAME/KEY: SITE
<222> LOCATION: (8)
<223> OTHER INFORMATION: Xaa = Glu or Cys
<220> FEATURE:
<221> NAME/KEY: SITE
<222> LOCATION: (18)
<223> OTHER INFORMATION: Xaa = Ala or Cys
<220> FEATURE:
<221> NAME/KEY: SITE
<222> LOCATION: (49)
<223> OTHER INFORMATION: Xaa = Gln or Cys
<220> FEATURE:
<221> NAME/KEY: SITE
<222> LOCATION: (81)
<223> OTHER INFORMATION: Xaa = Lys or Cys
<220> FEATURE:
<221> NAME/KEY: SITE
<222> LOCATION: (96)
<223> OTHER INFORMATION: Xaa = Leu or Cys
<220> FEATURE:
<221> NAME/KEY: SITE
<222> LOCATION: (70)
<223> OTHER INFORMATION: Xaa = Ser or Cys
<220> FEATURE:
<221> NAME/KEY: SITE
<222> LOCATION: (112)
<223> OTHER INFORMATION: Xaa = His or Cys
<220> FEATURE:
<221> NAME/KEY: SITE
<222> LOCATION: (121)
<223> OTHER INFORMATION: Xaa = Leu or Cys
<220> FEATURE:
<221> NAME/KEY: SITE
<222> LOCATION: (135)..(143)
<223> OTHER INFORMATION: Some or all of these residues may be missing
      beginning with the c-terminal end of the protein.

<400> SEQUENCE: 3

```
Met Gln Asp Pro Tyr Val Lys Xaa Ala Glu Asn Leu Lys Lys Tyr Phe
  1               5                  10                  15

Asn Xaa Gly His Ser Asp Val Ala Asp Asn Gly Thr Leu Phe Leu Gly
             20                  25                  30

Ile Leu Lys Asn Trp Lys Glu Glu Ser Asp Arg Lys Ile Met Gln Ser
         35                  40                  45

Xaa Ile Val Ser Phe Tyr Phe Lys Leu Phe Lys Asn Phe Lys Asp Asp
     50                  55                  60

Gln Ser Ile Gln Lys Xaa Val Glu Thr Ile Lys Glu Asp Met Asn Val
 65                  70                  75                  80

Xaa Phe Phe Asn Ser Asn Lys Lys Arg Asp Asp Phe Glu Lys Xaa
                 85                  90                  95

Thr Asn Tyr Ser Val Thr Asp Leu Asn Val Gln Arg Lys Ala Ile Xaa
            100                 105                 110
```

```
              100                 105                 110
Glu Leu Ile Gln Val Met Ala Glu Xaa Ser Pro Ala Ala Lys Thr Gly
      115                 120                 125

Lys Arg Lys Arg Ser Gln Met Leu Phe Arg Gly Arg Arg Ala Ser
  130                 135                 140
```

<210> SEQ ID NO 4
<211> LENGTH: 29
<212> TYPE: DNA
<213> ORGANISM: Homo sapiens

<400> SEQUENCE: 4
taaggttttc tgcacatttt acatatggg                              29

<210> SEQ ID NO 5
<211> LENGTH: 29
<212> TYPE: DNA
<213> ORGANISM: Homo sapiens

<400> SEQUENCE: 5
taaggttttc tgcgcatttt acatatggg                              29

<210> SEQ ID NO 6
<211> LENGTH: 29
<212> TYPE: DNA
<213> ORGANISM: Homo sapiens

<400> SEQUENCE: 6
tgatggtctc cacacacttt tggatgctc                              29

<210> SEQ ID NO 7
<211> LENGTH: 29
<212> TYPE: DNA
<213> ORGANISM: Homo sapiens

<400> SEQUENCE: 7
tgatggtctc cacgcacttt tggatgctc                              29

<210> SEQ ID NO 8
<211> LENGTH: 29
<212> TYPE: DNA
<213> ORGANISM: Homo sapiens

<400> SEQUENCE: 8
catctgaatg accgcaatta aaatatttc                              29

<210> SEQ ID NO 9
<211> LENGTH: 29
<212> TYPE: DNA
<213> ORGANISM: Homo sapiens

<400> SEQUENCE: 9
catctgaatg accacaatta aaatatttc                              29

<210> SEQ ID NO 10
<211> LENGTH: 29
<212> TYPE: DNA
<213> ORGANISM: Homo sapiens

<400> SEQUENCE: 10
acttggatga gttcgcatat tgctttgcg                              29

```
<210> SEQ ID NO 11
<211> LENGTH: 29
<212> TYPE: DNA
<213> ORGANISM: Homo sapiens

<400> SEQUENCE: 11
acttggatga gttcacatat tgctttgcg                              29

<210> SEQ ID NO 12
<211> LENGTH: 29
<212> TYPE: DNA
<213> ORGANISM: Homo sapiens

<400> SEQUENCE: 12
tgctattgaa aaacagaca ttcatgtct                               29

<210> SEQ ID NO 13
<211> LENGTH: 29
<212> TYPE: DNA
<213> ORGANISM: Homo sapiens

<400> SEQUENCE: 13
tgctattgaa aaagcagaca ttcatgtct                              29

<210> SEQ ID NO 14
<211> LENGTH: 29
<212> TYPE: DNA
<213> ORGANISM: Homo sapiens

<400> SEQUENCE: 14
tagctgctgg cgaacattca gccatcact                              29

<210> SEQ ID NO 15
<211> LENGTH: 29
<212> TYPE: DNA
<213> ORGANISM: Homo sapiens

<400> SEQUENCE: 15
tagctgctgg cgagcattca gccatcact                              29

<210> SEQ ID NO 16
<211> LENGTH: 29
<212> TYPE: DNA
<213> ORGANISM: Homo sapiens

<400> SEQUENCE: 16
aaaaggagac aatgcagctc tgcattatt                              29

<210> SEQ ID NO 17
<211> LENGTH: 29
<212> TYPE: DNA
<213> ORGANISM: Homo sapiens

<400> SEQUENCE: 17
aaaaggagac aatacagctc tgcattatt                              29

<210> SEQ ID NO 18
<211> LENGTH: 29
<212> TYPE: DNA
<213> ORGANISM: Homo sapiens

<400> SEQUENCE: 18
ccgaataatt agtgcacttt tcgaagtca                              29
```

```
<210> SEQ ID NO 19
<211> LENGTH: 29
<212> TYPE: DNA
<213> ORGANISM: Homo sapiens

<400> SEQUENCE: 19
ccgaataatt agtacacttt tcgaagtca                                    29
```